(12) United States Patent
Deng et al.

(10) Patent No.: US 7,776,597 B2
(45) Date of Patent: Aug. 17, 2010

(54) METHOD OF INDUCING EMBRYONIC STEM CELLS INTO PANCREATIC CELLS

(75) Inventors: Hongkui Deng, Beijing (CN); Mingxiao Ding, Beijing (CN); Yan Shi, Beijing (CN); Wei Jiang, Beijing (CN); Lingling Hou, Beijing (CN); Fuchou Tang, Cambridge (GB)

(73) Assignee: Beijing Hua Yuan Bo Chuang Technology Limited, Beijing (CN)

( * ) Notice: Subject to any disclaimer, the term of this patent is extended or adjusted under 35 U.S.C. 154(b) by 0 days.

(21) Appl. No.: 11/911,378

(22) PCT Filed: Apr. 14, 2006

(86) PCT No.: PCT/CN2006/000683

§ 371 (c)(1),
(2), (4) Date: Dec. 14, 2007

(87) PCT Pub. No.: WO2006/008361

PCT Pub. Date: Oct. 19, 2006

(65) Prior Publication Data

US 2008/0286867 A1    Nov. 20, 2008

(30) Foreign Application Priority Data

Apr. 15, 2005  (CN)  .................. 2005 1 0064431

(51) Int. Cl.
*C12N 5/00* (2006.01)
*C12N 5/02* (2006.01)
*C12N 5/071* (2006.01)

(52) U.S. Cl. .................. 435/377; 435/325; 435/366; 435/384

(58) Field of Classification Search .................. 435/325, 435/377, 366, 384
See application file for complete search history.

(56) References Cited

U.S. PATENT DOCUMENTS

2003/0138948 A1 *  7/2003  Fisk et al. ................ 435/366

FOREIGN PATENT DOCUMENTS

| CN | 1580246 | 2/2005 |
|---|---|---|
| JP | 2003-009854 | 1/2003 |
| WO | 02/059278 | 8/2002 |

OTHER PUBLICATIONS

Wheeler. Theriogenology. 2001, (56), 1345-1369.*
Smith et al. J. of Biotechnology, 99:1-22, 2002.*
Kania et al. Int. J. Dev. Bio., 48: 1061-1064, 2004.*
Skoudy et al. Biochem. J., 379: 749-756, May 1, 2004.*
Xu et al. Nature Biotech., 19: 971-974, 2001.*
BD Biosciences, BD Matrigel, accessed online at www.bdbiosciences.com, Oct. 30, 2009.*
International Search Report mailed Jul. 3, 2006, by The State Intellectual Property Office (SIPO) for International Application No. PCT/CN2006/000683 (previously filed with the Application on Oct. 12, 2007) (4 pages).
Yan Shi, et al., "Inducing Embryonic Stem Cells to Differentiate into Pancreatic b Cells by a Novel Three-Step Approach with Activin A and All-Trans Retinoic Acid"; Stem Cells, 2005; 23:656-662; May 5, 2005; see whole document (7 pages).
Liu, Xing-xia, et al., "The conditions of embryonic stem cells that are induced into insulin-secreting cells"; Journal of Shandong University Health Science, vol. 42, No. 1; pp. 118-122; Feb. 29, 2004; see the whole document (4 pages).
Kumakura, Hideaki, et al.; IP-103 Differentiation of Mouse Embryonic Stem Cells Into Pancreatic Islet Beta Cells in Vitro; Cell Structure and Function, 28(4):341; Aug. 1, 2003; see the whole document (1 page).

* cited by examiner

*Primary Examiner*—Thaian N Ton
(74) *Attorney, Agent, or Firm*—Osha • Liang LLP

(57) ABSTRACT

The present invention provided a simple three-step approach based on the combinational induction with activin A, all-trans retinoic acid and, optionally, other maturation factors which are able to induce embryonic stem cells to differentiate into insulin-producing cells. A kit used to induce embryonic stem cells to differentiate into insulin-producing cells was also provided.

7 Claims, 9 Drawing Sheets

Figure 6. hES cells induction protocol.
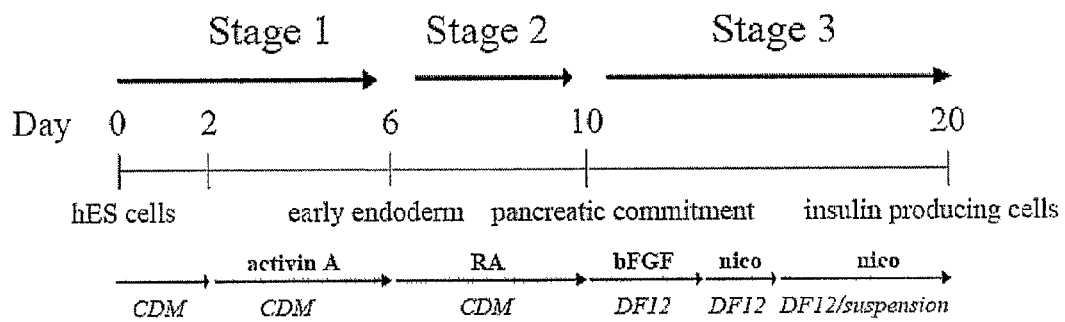
Figure 7. The expressions of the following genes were detected by RT-PCR: *sox17, pdx1, hlxb9, hnf4α, insulin, glut2, amylase(Amy), somastatin (SST), Sur1, glucagons (GCG), glucokinase(GCK)*.
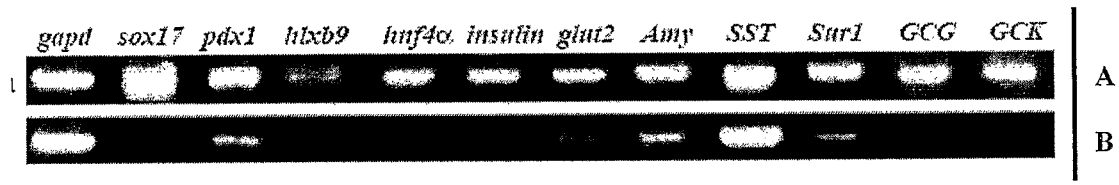
A. gene expression of hES which are induced by CDM act/RA protocol
B. gene expression of hES which are cultured by CDM only as control Figure 8. Immunostaining indicated that the terminally differentiated cells expressed pancreatic endocrine markers including pdx1, C-peptide, glucagon and somatostatin and exocrine marker amylase.

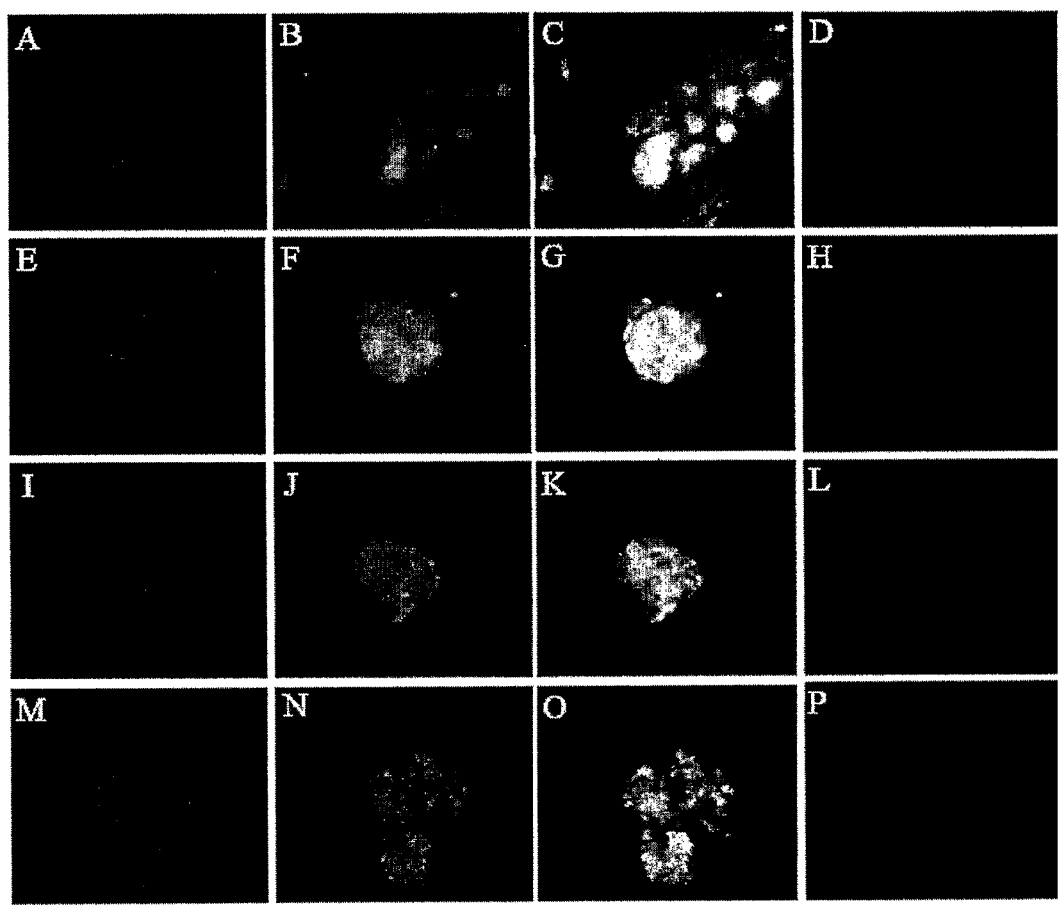

A-D. The final induced hES cells expressed C-peptide (A) and Pdx1 (B) (400×), merged in C and DAPI in D.

E-H. The final induced hES cells expressed glucagon (E) and C-peptide (F), merged in G and DAPI inH.

I-L. The final induced hES cells expressed amylase (I) and C-peptide (J) (400×), merged in K and DAPI in L.

M-P. The final induced hES cells expressed C-peptide (M) and somatostatin (N) (400×), merged in O and DAPI in P.

Figure 9. The secretion of insulin and C-peptide release by the terminally differentiated cells was responsive to the glucose level. The suspension culture was more efficient at inducing maturation of islet-like cells than the adhesion culture.

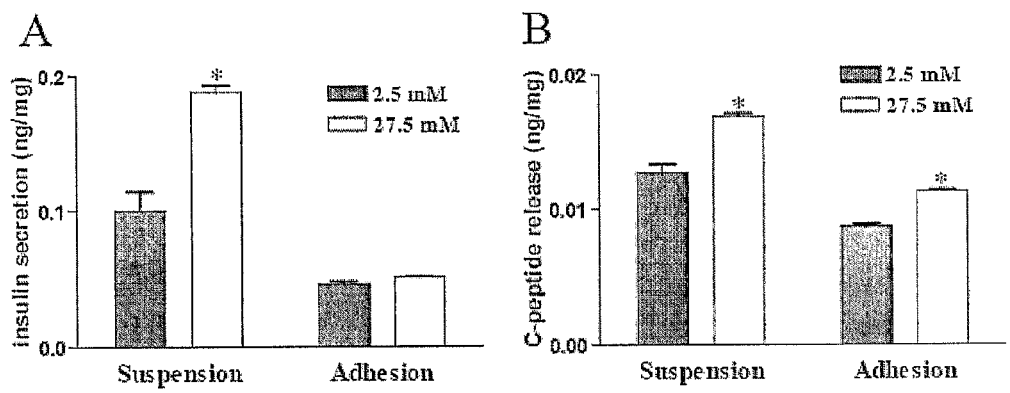

Figure 10. Transplantation of the induced hES cells partially ameliorates diabetic symptoms.

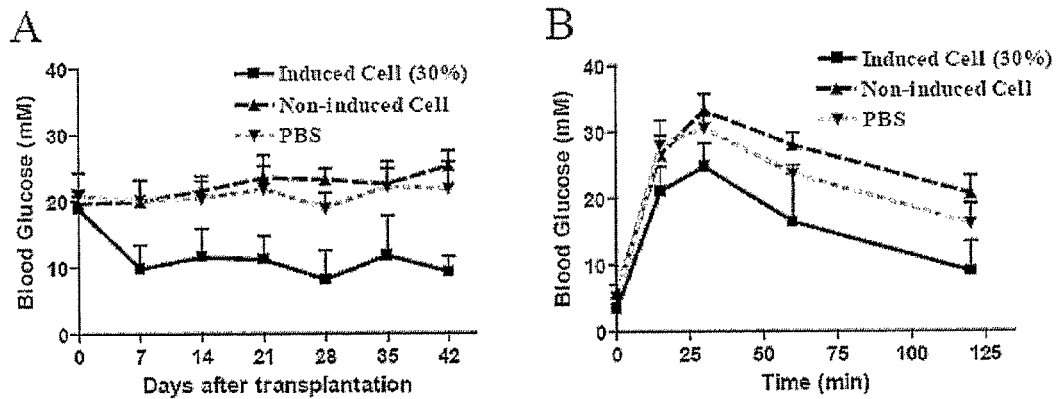

A. The blood glucose of 30% of the induced cell-transplanted diabetic nude mice (n=3) was decreased compared to the PBS (n=6) or non-induced cell (n=5) transplanted mice.
B. The intraperitoneal glucose tolerance test in the operated mice one month after the induced cell, non-induced cell and PBS transplantation.

Figure 11. Induced hES cells were transplanted into nude mice kidney capsule. After one month, the human C-peptide expression by double stain of human C-peptide and human nuclear specific antibody in renal capsule of transplanted nude mice were detected.

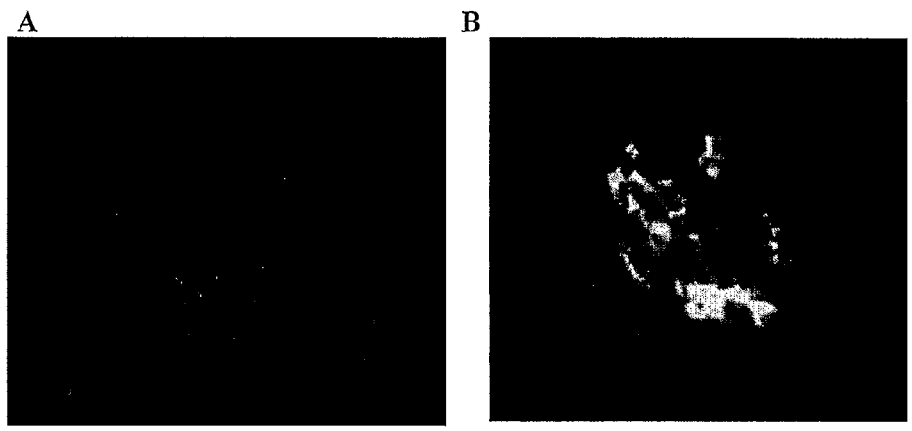

A. Induced hES cells transplanted into nude mice renal capsule expressed human C-peptide (400×).

B. The C-peptide positive cells are derived from human ES cells, which were demonstrated by human nuclear specific antibody staining (400×).

SEQUENCE LISTING

```
<160> NUMBER OF SEQ ID NOS: 38

<210> SEQ ID NO 1
<211> LENGTH: 22
<212> TYPE: DNA
<213> ORGANISM: artificial sequence
<220> FEATURE:
<223> OTHER INFORMATION: primer

<400> SEQUENCE: 1
tagtgaccag ctataatcag ag                                             22

<210> SEQ ID NO 2
<211> LENGTH: 20
<212> TYPE: DNA
<213> ORGANISM: artificial sequence
<220> FEATURE:
<223> OTHER INFORMATION: primer

<400> SEQUENCE: 2
acgccaaggt ctgaaggtcc                                                20
```

<210> SEQ ID NO 3
<211> LENGTH: 20
<212> TYPE: DNA
<213> ORGANISM: artificial sequence
<220> FEATURE:
<223> OTHER INFORMATION: primer

<400> SEQUENCE: 3
acctgagtcc gagtctgacc                                                    20

<210> SEQ ID NO 4
<211> LENGTH: 20
<212> TYPE: DNA
<213> ORGANISM: artificial sequence
<220> FEATURE:
<223> OTHER INFORMATION: primer

<400> SEQUENCE: 4
ggcaccttga gaaagcagtc                                                    20

<210> SEQ ID NO 5
<211> LENGTH: 25
<212> TYPE: DNA
<213> ORGANISM: artificial sequence
<220> FEATURE:
<223> OTHER INFORMATION: primer

<400> SEQUENCE: 5
cttagcgtgt cgccacagcc ctcca                                              25

<210> SEQ ID NO 6
<211> LENGTH: 25
<212> TYPE: DNA
<213> ORGANISM: artificial sequence
<220> FEATURE:
<223> OTHER INFORMATION: primer

<400> SEQUENCE: 6
tccaacagcc gcctttcgtt attct                                              25

<210> SEQ ID NO 7
<211> LENGTH: 20
<212> TYPE: DNA
<213> ORGANISM: artificial sequence
<220> FEATURE:
<223> OTHER INFORMATION: primer

<400> SEQUENCE: 7
ggataaattc gcctggatga                                                    20

<210> SEQ ID NO 8
<211> LENGTH: 20
<212> TYPE: DNA
<213> ORGANISM: artificial sequence
<220> FEATURE:
<223> OTHER INFORMATION: primer

<400> SEQUENCE: 8
ttcctttggt ttctggaact                                                    20

<210> SEQ ID NO 9
<211> LENGTH: 23
<212> TYPE: DNA
<213> ORGANISM: artificial sequence
<220> FEATURE:

-continued

<223> OTHER INFORMATION: primer

<400> SEQUENCE: 9
atttgccacc tagccacagc acc                                      23

<210> SEQ ID NO 10
<211> LENGTH: 23
<212> TYPE: DNA
<213> ORGANISM: artificial sequence
<220> FEATURE:
<223> OTHER INFORMATION: primer

<400> SEQUENCE: 10
cgcatttgat cccgtacaac ctg                                      23

<210> SEQ ID NO 11
<211> LENGTH: 25
<212> TYPE: DNA
<213> ORGANISM: artificial sequence
<220> FEATURE:
<223> OTHER INFORMATION: primer

<400> SEQUENCE: 11
cctgaaccct aaggccaacc gtgaa                                    25

<210> SEQ ID NO 12
<211> LENGTH: 25
<212> TYPE: DNA
<213> ORGANISM: artificial sequence
<220> FEATURE:
<223> OTHER INFORMATION: primer

<400> SEQUENCE: 12
atacccaaga aggaaggctg gaaaa                                    25

<210> SEQ ID NO 13
<211> LENGTH: 18
<212> TYPE: DNA
<213> ORGANISM: artificial sequence
<220> FEATURE:
<223> OTHER INFORMATION: primer

<400> SEQUENCE: 13
acacgtcccc atctgaag                                            18

<210> SEQ ID NO 14
<211> LENGTH: 18
<212> TYPE: DNA
<213> ORGANISM: artificial sequence
<220> FEATURE:
<223> OTHER INFORMATION: primer

<400> SEQUENCE: 14
cttccttctt catgccag                                            18

<210> SEQ ID NO 15
<211> LENGTH: 20
<212> TYPE: DNA
<213> ORGANISM: artificial sequence
<220> FEATURE:
<223> OTHER INFORMATION: primer

<400> SEQUENCE: 15
gtcattgaga gcaatgccag                                          20

```
<210> SEQ ID NO 16
<211> LENGTH: 20
<212> TYPE: DNA
<213> ORGANISM: artificial sequence
<220> FEATURE:
<223> OTHER INFORMATION: primer

<400> SEQUENCE: 16
gtgttcctac ccccaatgtg                                                     20

<210> SEQ ID NO 17
<211> LENGTH: 22
<212> TYPE: DNA
<213> ORGANISM: artificial sequence
<220> FEATURE:
<223> OTHER INFORMATION: primer

<400> SEQUENCE: 17
cagtgacgac cagagccaga cc                                                  22

<210> SEQ ID NO 18
<211> LENGTH: 21
<212> TYPE: DNA
<213> ORGANISM: artificial sequence
<220> FEATURE:
<223> OTHER INFORMATION: primer

<400> SEQUENCE: 18
ccacgacttg cccagcatct t                                                   21

<210> SEQ ID NO 19
<211> LENGTH: 21
<212> TYPE: DNA
<213> ORGANISM: artificial sequence
<220> FEATURE:
<223> OTHER INFORMATION: primer

<400> SEQUENCE: 19
accaaagctc acgcgtggaa a                                                   21

<210> SEQ ID NO 20
<211> LENGTH: 22
<212> TYPE: DNA
<213> ORGANISM: artificial sequence
<220> FEATURE:
<223> OTHER INFORMATION: primer

<400> SEQUENCE: 20
tgatgtgtct ctcggtcaag tt                                                  22

<210> SEQ ID NO 21
<211> LENGTH: 25
<212> TYPE: DNA
<213> ORGANISM: artificial sequence
<220> FEATURE:
<223> OTHER INFORMATION: primer

<400> SEQUENCE: 21
cctaagatgc ccgacttcaa ctccc                                               25

<210> SEQ ID NO 22
<211> LENGTH: 24
<212> TYPE: DNA
<213> ORGANISM: artificial sequence
<220> FEATURE:
<223> OTHER INFORMATION: primer
```

```
<400> SEQUENCE: 22
gcccttctgt ttctccgctt cctg                                          24

<210> SEQ ID NO 23
<211> LENGTH: 22
<212> TYPE: DNA
<213> ORGANISM: artificial sequence
<220> FEATURE:
<223> OTHER INFORMATION: primer

<400> SEQUENCE: 23
atcagaaggc accaacctca ac                                            22

<210> SEQ ID NO 24
<211> LENGTH: 21
<212> TYPE: DNA
<213> ORGANISM: artificial sequence
<220> FEATURE:
<223> OTHER INFORMATION: primer

<400> SEQUENCE: 24
tgtctttgtc caccacgcac t                                             21

<210> SEQ ID NO 25
<211> LENGTH: 21
<212> TYPE: DNA
<213> ORGANISM: artificial sequence
<220> FEATURE:
<223> OTHER INFORMATION: primer

<400> SEQUENCE: 25
gaggccatca agcaccatca c                                             21

<210> SEQ ID NO 26
<211> LENGTH: 20
<212> TYPE: DNA
<213> ORGANISM: artificial sequence
<220> FEATURE:
<223> OTHER INFORMATION: primer

<400> SEQUENCE: 26
ggctgcgtct agttgcagta                                               20

<210> SEQ ID NO 27
<211> LENGTH: 20
<212> TYPE: DNA
<213> ORGANISM: artificial sequence
<220> FEATURE:
<223> OTHER INFORMATION: primer

<400> SEQUENCE: 27
gctaccgaca gcctattcta                                               20

<210> SEQ ID NO 28
<211> LENGTH: 19
<212> TYPE: DNA
<213> ORGANISM: artificial sequence
<220> FEATURE:
<223> OTHER INFORMATION: primer

<400> SEQUENCE: 28
caagtccact gacatgaag                                                19

<210> SEQ ID NO 29
<211> LENGTH: 19
```

```
<212> TYPE: DNA
<213> ORGANISM: artificial sequence
<220> FEATURE:
<223> OTHER INFORMATION: primer

<400> SEQUENCE: 29
ctgacaactt caaagcaaa                                                  19

<210> SEQ ID NO 30
<211> LENGTH: 22
<212> TYPE: DNA
<213> ORGANISM: artificial sequence
<220> FEATURE:
<223> OTHER INFORMATION: primer

<400> SEQUENCE: 30
tacagcatcc acataaatac ga                                              22

<210> SEQ ID NO 31
<211> LENGTH: 20
<212> TYPE: DNA
<213> ORGANISM: artificial sequence
<220> FEATURE:
<223> OTHER INFORMATION: primer

<400> SEQUENCE: 31
gatgctgtcc tgccgcctcc                                                 20

<210> SEQ ID NO 32
<211> LENGTH: 18
<212> TYPE: DNA
<213> ORGANISM: artificial sequence
<220> FEATURE:
<223> OTHER INFORMATION: primer

<400> SEQUENCE: 32
tgccatagcc gggtttga                                                   18

<210> SEQ ID NO 33
<211> LENGTH: 20
<212> TYPE: DNA
<213> ORGANISM: artificial sequence
<220> FEATURE:
<223> OTHER INFORMATION: primer

<400> SEQUENCE: 33
ttgccgaaac cgtagaagga                                                 20

<210> SEQ ID NO 34
<211> LENGTH: 21
<212> TYPE: DNA
<213> ORGANISM: artificial sequence
<220> FEATURE:
<223> OTHER INFORMATION: primer

<400> SEQUENCE: 34
ttggagacca ttagggcgta g                                               21

<210> SEQ ID NO 35
<211> LENGTH: 19
<212> TYPE: DNA
<213> ORGANISM: artificial sequence
<220> FEATURE:
<223> OTHER INFORMATION: primer

<400> SEQUENCE: 35
```

-continued

```
aggcagaccc actcagtga                                            19

<210> SEQ ID NO 36
<211> LENGTH: 20
<212> TYPE: DNA
<213> ORGANISM: artificial sequence
<220> FEATURE:
<223> OTHER INFORMATION: primer

<400> SEQUENCE: 36
aacaatggcg acctcttctg                                           20

<210> SEQ ID NO 37
<211> LENGTH: 19
<212> TYPE: DNA
<213> ORGANISM: artificial sequence
<220> FEATURE:
<223> OTHER INFORMATION: primer

<400> SEQUENCE: 37
agggaatgct tgccgactc                                            19

<210> SEQ ID NO 38
<211> LENGTH: 19
<212> TYPE: DNA
<213> ORGANISM: artificial sequence
<220> FEATURE:
<223> OTHER INFORMATION: primer

<400> SEQUENCE: 38
cactggcctc ttcatgggt                                            19
```

METHOD OF INDUCING EMBRYONIC STEM CELLS INTO PANCREATIC CELLS

RELATED APPLICATIONS

This application is a U.S. National Phase of International Application No. PCT/CN2006/000683, filed Apr. 14, 2006, designating the U.S. and published in English on Oct. 19, 2006 as WO 2006/108361, which claims the benefit of Chinese application No. 200510064431.5, filed Apr. 15, 2005.

BACKGROUND OF THE INVENTION

1. Field of the Invention

This invention relates generally to a method of inducing embryonic stem cells. Particularly, the present invention relates to a method for inducing embryonic stem cells into pancreatic cells, and a kit with the same use.

2. Description of the Prior Art

As the most common metabolic disorder diseases in human, Diabetes Mellitus affects 4 to 5% of the world population. The number of patients with diabetes is predicted to exceed 350 million by 2010. Type I diabetes mellitus results from the autoimmune destruction of the β cells in pancreatic islets. Many research groups are therefore exploring ways to replace these destroyed insulin-producing cells. Until now, pancreatic islet cell transplantation is the only effective approach to cure type I diabetes in addition to insulin injection(Serup P, Madsen O D, Mandrup-Poulsen T. Islet and stem cell transplantation for treating diabetes. BMJ 2001; 322: 29-32). However, this method could not be widely utilized due to the severe shortage of transplantable donor islets.

Functional β cell obtained from embryonic stem (ES) cells has been considered to solve the problem of the shortage of transplantable islets: ES cells have been shown to be able to differentiate into pancreatic islet-like clusters, especially pancreatic β cells' (Soria B, Roche E, Berna G, et al. Insulin-secreting cells derived from embryonic stem cells normalize glycemia in streptozotocin-induced diabetic mice. Diabetes 2000; 49(2):157-162; Lumelsky N, Blondel O, Laeng P, et al. Differentiation of embryonic stem cells to insulin-secreting structures similar to pancreatic islets. Science 2001; 292: 1389-1394; Assady S, Maor G, Amit M, et al. Insulin production by human embryonic stem cells. Diabetes 2001; 50(8): 1691-169.). Soria et al., for the first time, successfully induced ES cells to differentiate into pancreatic β cells by a cell-trapping system (Soria B, Roche E, Berna G, et al. Insulin-secreting cells derived from embryonic stem cells normalize glycemia in streptozotocin-induced diabetic mice. Diabetes 2000; 49(2):157-162). This method, however, is a complicated process involving genetic manipulation. Lumelsky et al (Lumelsky N, Blondel O, Laeng P, et al. Differentiation of embryonic stem cells to insulin-secreting structures similar to pancreatic islets. Science 2001; 292:1389-1394) came up with a five-stage method to induce ES cells to differentiate into insulin-producing islet-like structures without genetic modification. Hori et al (Hori Y, Rulifson I C, Tsai B C, et al. Growth inhibitors promote differentiation of insulin-producing tissue from embryonic stem cells. Proc Natl Acad Sci USA 2002; 99(25):16105-16110) and Blyszczuk et al (Blyszczuk P, Czyz J, Kania G, et al. Expression of Pax4 in embryonic stem cells promotes differentiation of nestin-positive progenitor and insulin-producing cells. Proc NatI Acad Sci USA 2003; 100(3):998-1003) improved Lumelsky's five-stage method by adding growth inhibitor LY294002 or over-expressing pax4 gene. Nonetheless, all these induction approaches are complicated in certain aspects and take a long period of time. Hansson et al, (Blyszczuk P, Czyz J, Kania G, et al. Expression of Pax4 in embryonic stem cells promotes differentiation of nestin-positive progenitor and insulin-producing cells. Proc Natl Acad Sci USA 2003; 100(3):998-1003), after using the five-stage method, found that the absorbance of insulin from the culture medium by ES cell may lead to false positive result. Therefore, what is needed is to find the specific induction factors that can induce ES cells to differentiate into pancreatic β cells in an easy and fast approach. Some factors have been reported to have the ability to promote the differentiation of definitive endoderm. Activin A, a member of TGF-β superfamily, is critical for mesoderm and endoderm formation during gastrulation. When used at a high concentration, it substantially induces endoderm formation (Kumar M, Jordan N, Melton DA, et al. Signals from lateral plate mesoderm instruct endoderm toward a pancreatic fate. Developmental Biology 2003; 259: 109-122; Hill CS. TGF-β signalling pathways in early Xenopus development. Curr Opin Genet Dev 2001; 11(5):533-540). All-trans retinoic acid (RA) is a well-characterized signaling molecule that acts in anteroposterior patterning of neuroectoderm and mesoderm in vertebrates (Maden M. Role and distribution of retinoic acid during CNS development. Int Rev Cytol 2001; 209:1-77). Current evidence indicates that RA is also involved in the regulation of the embryonic endoderm differentiation pattern especially in the early pancreas bud formation and it can also improve insulin expression in pancreatic β cells and INS-1 cell line (Stafford D, Prince V E. Retinoic Acid signaling is required for a critical early step in Zebrafish pancreatic development. Current Biology 2002; 12(14):1215-1220; Blumentrath J, Neye H, Verspohl E J. Effects of retinoids and thiazolidinediones on proliferation, insulin release, insulin mRNA, GLUT2 transporter protein and mRNA of INS-1 cells. Cell Biochem Funct 2001; 19:159-169). It has been demonstrated that the combination of activin A and RA was able to induce Xenopus presumptive ectoderm region of the blastula to differentiate into pancreatic insulin-positive cells (Moriya N, Komazaki S, Takahashi S, et al. In vitro pancreas formation from Xenopus ectoderm treated with activin and retinoic acid. Develop Growth Differ 2000; 42:593-602).

SUMMARY OF THE INVENTION

It is an object of the present invention to provide a method for inducing embryonic stem cells into pancreatic cells. It is another object of the present invention to provide a kit used for inducing embryonic stem cells into pancreatic cells.

The present invention achieves these and other objectives by providing a method of inducing embryonic stem cell, comprising in sequence the steps of:

culturing embryonic stem cells in a cell culture medium to form embryonic bodies;

incubating the embryonic bodies with Activin A; and incubating the embryonic bodies with All-trans retinoic acid (RA) to develop insulin-producing precursor cells.

In one aspect, the culture medium used in the method is DMEM containing about 10% fetus calf serum when embryonic stem cells are from mice. In another aspect, the culture medium is CDM when embryonic stem cells are from human.

In one aspect, the concentration of Activin A is about 50-300 ng/ml culture medium; and the concentration of RA is about $1 \times 10^{-7} - 1 \times 10^{-5}$ mol/L culture medium.

In one embodiment, the method further comprises a step of incubating the embryonic bodies in a culture medium coated with Metrigel before incubating the embryonic bodies with Activin A. In one aspect, the mass percentage of the metrigel in the culture medium is about 1%.

In another embodiment, the embryonic bodies are incubated with Activin A for 20 hours-4 days, then cultured in a culture medium without Activin A for 6-8 hours, and then incubated with RA for 20 hours-4 days to develop insulin-producing precursor cells.

In another embodiment, the method further comprises a step of incubating the resultant insulin-producing precursor cells in a culture medium containing maturation factor(s) to expand insulin-producing precursor cells. In one embodiment, the maturation factor is bFGF with a concentration of 8-12 ng/ml.

In another embodiment, the method further comprises a step of incubating the expanded insulin-producing precursor cells in a culture medium containing N2 supplement, B27 supplement, Laminin, and nicotinamide to develop insulin producing cells. In one aspect, the culture medium is DMEM/F12 or CDM containing N2 supplement (1:100, commercially available from Gibco), B27 supplement (1:50, commercially available from Gibco), 1 µg/ml of Laminin, 10 ng/ml of bFGF, Insulin-Transferrin-Selenium-A (1:100, commercially available form Gibco) and 10 mmol/L of nicotinamide.

The present invention further provided a kit for inducing embryonic stem cell differentiation.

In one embodiment, the kit comprises Activin A and RA. In another embodiment, the kit further comprises Metrigel. In yet another embodiment, the kit further comprises serum and/or a first culture medium. In one aspect, the Metrigel was coated on the first culture medium. In another aspect, the Metrigel is provided separately. In further another aspect, the first culture medium contains maturation factors such as bFGF. In another embodiment, the kit further contains a second culture medium comprising bFGF.

BRIEF DESCRIPTION OF THE DRAWINGS

FIG. 6 is a chart showing human Embryonic Stem (hES) cells induction approach.

FIG. 7A shows the marker gene expressions of hES which are induced by CDM act/RA approach.

FIG. 7B shows the marker gene expressions of hES which are cultured by CDM only as control.

FIGS. 8A-D are pictures showing the final induced hES cells expressed C-peptide and Pdx1 (400×).

FIGS. 8 E-H are pictures showing the final induced hES cells expressed glucagon and C-peptide.

FIGS. 8 I-L are pictures showing the final induced hES cells expressed amylase and C-peptide (400×).

FIGS. 8 M-P are pictures showing the final induced hES cells expressed C-peptide and somatostatin.

FIG. 9A is a comparison of terminally differentiated cells for insulin secretion between suspension culture and adhesion culture.

FIG. 9B is a comparison of terminally differentiated cells for C-peptide release between suspension culture and adhesion culture.

FIG. 10A is the result of blood glucose level comparison among induced cell-transplanted diabetic nude mice, PBS transplanted mice, and non-induced cell transplanted mice.

FIG. 10B is the result of intraperitoneal glucose tolerance test in the operated mice one FIG. 11A is a picture showing human C-peptide expression in induced cells (400×)

FIG. 11B shows the result of human nuclear specific antibody staining, indicating C-peptide positive cells are derived from human ES cells (400×).

DETAILED DESCRIPTION OF THE PREFERRED EMBODIMENT

Figure 1:
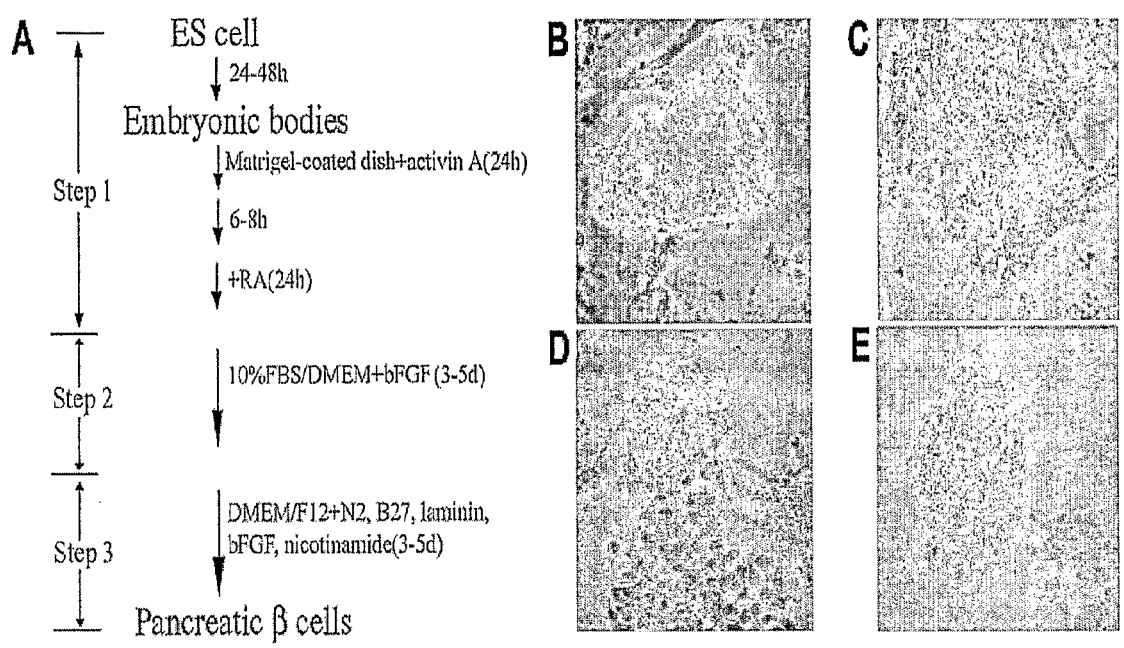
FIG. 1A shows the three-step method provided in the present invention which can induce ES cells to differentiate into insulin-positive cells.
FIG. 1B is a picture showing the formation of EB cell cluster of mice ES-R1 cell.
FIG. 1C is a picture showing epithelial-like construction of pancreatic precursor cells in step 2 of the three-step approach.
FIG. 1D-1E are pictures showing cluster-like construction of cultured cells in step 3 of the three-step approach.

Previous studies showed that ES cells could be specifically induced to differentiate into pancreatic β cells (Blyszczuk P, Czyz J, Kania G, et al. Expression of Pax4 in embryonic stem cells promotes differentiation of nestin-positive progenitor and insulin-producing cells. Proc Natl Acad Sci USA 2003; 100(3):998-1003; Hansson M, Tonning A, Frandsen U, et al. Artifactual Insulin Release From Differentiated Embryonic Stem Cells. Diabetes 2004; 53:2603-2609). However, most of induction strategies took about one month to obtain insulin-positive cells. In this study, a novel three-step approach was developed based on combination of activin A, RA and other maturation factors such as matrigel, nicotinamide, basic fibroblast growth factor (bFGF). At the end of the third step of our approach, these induced cells form small islet-like clusters and express pancreatic β cell markers including insulin, pdx-1, glut2, isl1 and hnf3β, and can also rescue STZ-treated diabetic mice upon transplantation.

Three factors, i.e., activin A, RA and niatrigel, play important roles in our experimental induction of pancreatic β cells. Activin A is important for early definitive endoderm development. It is a disulfide-stabilized protein that belongs to the TGF-β superfamily. The binding of activin to the cell surface receptor can induce the expression of many genes including mixl1 and goosecoid, which is important for early endoderm development (Kumar M, Jordan N, Melton DA, et al. Signals from lateral plate mesoderin instruct endoderm toward a pancreatic fate. Developmental Biology 2003; 259: 109-122; Hill CS. TGF-P signalling pathways in early Xenopus development. Curr Opin Genet Dev 2001; 11(5):533-540). Kubo et al reported that activin A could induce ES cells to differentiate into definitive endoderm cells (Kubo A, Shinozaki K, Shannon J M, et al. Development of definitive endoderm from embryonic stem cells in culture. Development 2004; 131: 1651-1662). In addition, activin A can improve insulin secretion in cultured human pancreatic islets (Florio P, Luisi S, Marchetti P, et al. Activin A stimulates insulin secretion in cultured human pancreatic islets. J Endocrinol Invest 2000; 23(4):231-234) and regulate differentiation of pancreatic β cells during development and regeneration of β cells in diabetic neonatal rats (Lei L, Yi Z, Seno M, et al. Activin A and Betacellulin Effect on Regeneration of Pancreatic B-Cells in Neonatal Streptozotocin-Treated Rats. Diabetes 2004; 53:608-615). A combination of these functions of activin A can explain how the activin A works in our system. Second, it has been recently demonstrated that RA is an important signaling molecule in the development of the early embryonic pancreas in addition to functions on induction of ectoderm and mesoderm development (Maden M. Role and distribution of retinoic acid during CNS development. Int Rev Cytol 2001; 209:1-77). During zebrafish development, increased RA signaling can induce remarkable anterior expansion of the pancreas and liver endoderm. Conversely, inhibition of RA signaling by BMS493 inhibits early pancreas differentiation from embryonic endoderm (Stafford D, Prince VE. Retinoic Acid signaling is required for a critical early step in Zebrafish pancreatic development. Current Biology 2002; 12(14):1215-1220). Furthermore, Micallef et al. reported that RA could induce pdx1 positive endoderm formation when added at the fourth day of mouse embryonic stem cell differentiation (Micallef S J, Janes M E, Knezevic K, et al. Retinoic Acid Induces Pdx1-Positive Endoderm in Differentiating Mouse Embryonic Stem Cells. Diabetes 2004 Dec. 7 [Epub ahead of print]). For pancreas maturation, RA plays a role in the differentiation of endocrine and ductal cells, predominantly through paracrine actions and upregulation of pdx-1 gene (Tulachan S S, Doi R, Kawaguchi Y, et al. All-trans retinoic acid induces differentiation of ducts and endocrine cells by mesenchymal/epithelial interactions in embryonic pancreas. Diabetes 2003; 52(1):76-84). RA is also found to promote endocrine lineage at the expense of exocrine differentiation during dorsal pancreas development (Chen Y, Pan F C, Brandes N, et al. Retinoic acid signaling is essential for pancreas development and promotes endocrine at the expense of exocrine cell differentiation in Xenopus. Developmental Biology 2004; 271:144-160). Therefore, it is clear that RA can facilitate the development of pancreatic precursor cells and endocrine cells. During the time when ES cells differentiate toward endoderm lineage upon Activin A induction, RA will further promote endoderm lineage specialize into pancreatic progenitors. After activin A and RA induction, differentiated embryonic stem cells can express pancreatic progenitor markers such as pdx1, hnf3 α and hnf4 β. These data indicated that combination of activin A and RA was able to induce early pancreatic cell differentiation from embryonic stem cells. The present invention also demonstrated that induction with both activin A and RA is more efficient than with only one of the two factors. It has been demonstrated that matrigel functioned as an important extracellular matrix for pancreas differentiation and maturation in vitro. Matrigel, a mixture of extracellular matrix including laminin and growth factors such as FGF and TGF β, is essential for pancreatic progenitor cell migration, the formation of three dimensional cystic structures, and protrusion of islet bud (Gao R, Ustinov J, Pulkkinen M A, et al. Characterization of Endocrine Progenitor Cells and Critical Factors for Their Differentiation in Human Adult Pancreatic Cell Culture. Diabetes 2003; 52:2007-2015). Gittes G K et al also proved that laminin, one of the major components of matrigel, is involved in mouse embryonic pancreatic duct lineage selection (Jiang F X, Cram D S, DeAizpurua H J, et al. Laminin-1 promotes differentiation of fetal mouse pancreatic betacells. Diabetes 1999; 48:722-730; Crisera C A, Kadison A S, Breslow G D, et al. Expression and role of laminin-1 in mouse pancreatic organogenesis. Diabetes 2000; 49:936-944). Moreover, if human pancreatic ductal epithelial cells are cultured on the matrigel, they can form insulin-positive islet-like clusters (Bonner-Weir S, Taneja M, Weir G C, et al. In vitro cultivation of human islets from expanded ductal tissue. Proc Natl Acad Sci USA 2000; 97:7999-8004). The present invention demonstrated that matrigel was necessary for small islet-like cluster formation during induction. If ES cells were cultured on the laminin or gelatin matrix alone, cell clusters could not form well. As being further shown in the illustrative examples hereafter, differentiated cells grew better on matrigel than on laminin or gelatin, which indicates that matrigel can offer more induction factors than laminin or gelatin.

The present invention has provided a novel three-step approach with combination of activin A, RA, and optionally, other maturation factors which can induce ES cells to differentiate into functional insulin-producing cells in a short period. The results indicate TGF-β and RA signals are critical for pancreatic β cell development and maturation. The insulin positive cells can further express characteristic pancreatic β cell marker genes such as insulinI, pdx1, glut2, hnf3β and isl1. Moreover, by using vectors carrying reporter gene located downstream of insulin promoter, the present invention can reduce the false positive rate, thereby actually inducing ES cells to differentiate into insulin-producing cells. Further, as demonstrated by examples hereunder, the present invention can also rescue the streptozocin (STZ)-induced diabetic mice when being transplanted under renal capsules. The induction system described herein offers a new in vitro induction model for studying the mechanism of pancreatic β cell formation and differentiation, and provides a potential source of insulin-producing cells for transplantation therapy of type I diabetes mellitus.

Having now generally described the invention, the same will be more readily understood through reference to the following examples, which are provided by way of illustration and are not intended to be limiting of the present invention.

EXAMPLES

Example 1 Induction of Mice Embryonic Stem Cells into Pancreatic Cells

Unless specified, percentage used in the examples refers to mass percentage. A well-tested ES cell line, ES-R1 (Nagy A, Rossant J, Nagy R, et al. Derivation of completely cell culture-derived mice from early-passage embryonic stem cells. Proc. Natl. Acad. Sci. USA 1993; 90:8424-8428) was cultured in Dulbecco's Modified Eagle Medium (DMEM, Gibco-BRL) with 20% fetal bovine serum (FBS) (Gibco-BRL) and 1000 U/ml leukemia inhibitory factor (LIF, Gibco-BRL).

1. ES Cell Culture and Differentiation Conditions.

The approach of ES cells differentiating into pancreatic βcells (three step approach, see FIG. 1A) is as follows:

Step 1, to induce embryonic body (EB) formation, ES cells were dissociated with trypsin and suspended into Petri dishes (Alpha medical instrument) with 10% FBS/DMEM without LIF. After 24 to 48 hours (See FIG. 1B), EBs were collected and re-plated into 10% FBS/DMEM without LIF in 1% Matrigel (BD Biosciences) coated dishes. Two hours later, EBs began to spread onto the dishes and were cultured in 10% FBS/DMEM with 100 ng/ml activin A (Sigma) for 24 hours. Then EBs were switched to 10% FBS/DMEM for 6-8 hours as an interval. After this interval, the differentiated EB cells were cultured in 10% FBS/DMEM with $10^{-6}$ M RA (Sigma) for another 24 hours.

Step 2, to expand insulin-producing precursors, the differentiated EB cells were cultured in 10% FBS/DMEM with 10 ng/ml bFGF (Sigma) for 3-5 days, during which most cells showed epithelial-like construction (see FIG. 1C).

Step 3, to mature the insulin producing cells, the expanded cells in step 2 were switched to DMEM/F12 (Gibco-BRL) with N2 supplement (1:100, Gibco-BRL), B27 supplement (1:50 Gibco-BRL), 1 μg/ml Laminin (Sigma), 10 ng/ml bFGF (Sigma) and 10 mM nicotinamide (Sigma) and cultured for 3-5 days (Lumelsky N, Blondel O, Laeng P, et al. Differentiation of embryonic stem cells to insulin-secreting structures similar to pancreatic islets. Science 2001; 292:1389-1394.) The morphology of cells was observed under a Nikon phase-contrast microscope (TS-100). The results show the cultured cells formed cluster-like construction (see FIGS. 1D and 1E).

2. RT-PCR Analysis of Gene Expression in Differentiated Cells.

Total RNA was extracted by Catrimox-14 kit (TaKaRa) from the cells in step 2 or step 3 which were induced by both with and without activin A and RA or with only one of them. Then RNA was reverse-transcribed into cDNA by MMLV reverse transcriptase (Promega). PCR was performed with Ex Taq polymerase (TaKaRa) in PCR buffer. Cycle conditions were as follows: 94° C. for 5 min followed by 35 cycles (94° C. denaturation for 50 sec, 56-58° C. annealing for 30 sec, 72° C. elongation for 40 sec), with a final incubation at 72° C. for 4 min. PCR primers of pdx1, glut2, isl1, β-actin etc. were designed with Prime Premier 5.0. The sequences for the PCR primers (sense and antisense, respectively) are:

```
InsulinI:
TAGTGACCAGCTATAATCAGAG                    (SEQ ID No. 1)
and

ACGCCAAGGTCTGAAGGTCC (288 bp);           (SEQ ID No. 2)

hnf3β:
ACCTGAGTCCGAGTCTGACC                      (SEQ ID No. 3)
and

GGCACCTTGAGAAAGCAGTC (345 bp);           (SEQ ID No. 4)

pdx1:
CTTAGCGTGTCGCCACAGCCCTCCA                (SEQ ID No. 5)
and

TCCAACAGCCGCCTTTCGTTATTCT (472 bp);      (SEQ ID No. 6)

glut2:
GGATAAATTCGCCTGGATGA                     (SEQ ID No. 7)
and

TTCCTTTGGTTTCTGGAACT (299 bp);           (SEQ ID No. 8)

isl1:
ATTTGCCACCTAGCCACAGCACC                  (SEQ ID No. 9)
and

CGCATTTGATCCCGTACAACCTG (335 bp);        (SEQ ID No. 10)

β-actin:
CCTGAACCCTAAGGCCAACCGTGAA                (SEQ ID No. 11)
and

ATACCCAAGAAGGAAGGCTGGAAAA (480 bp);      (SEQ ID No. 12)

hnf4α:
ACACGTCCCCATCTGAAG                       (SEQ ID No. 13)
and

CTTCCTTCTTCATGCCAG (269 bp).             (SEQ ID No. 14)
```

Figure 2:
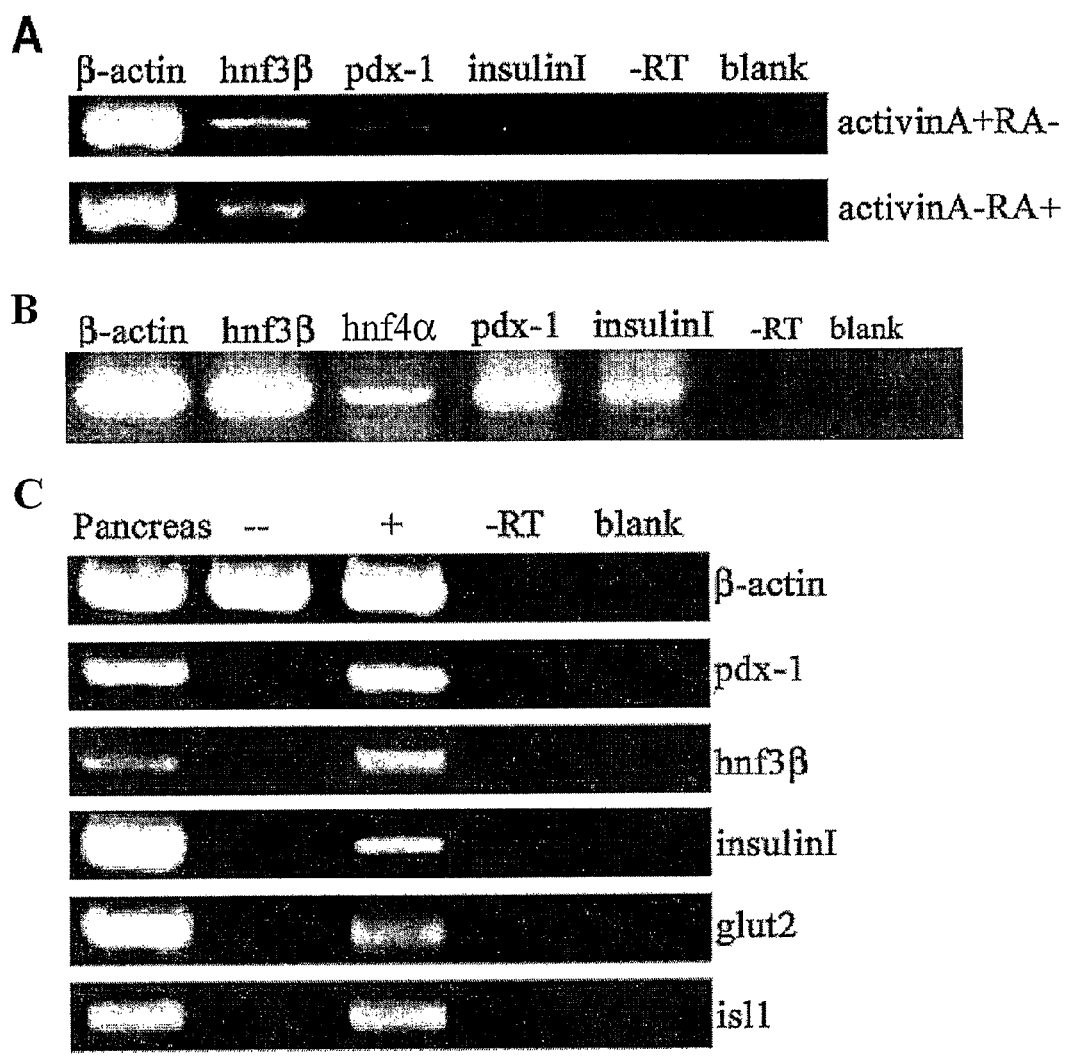
FIG. 2A shows the RT-PCR results of the expressions of the marker genes of differentiated cells induced by either activin or RA at the end of step 2.
FIG. 2B shows the RT-PCR results of the expressions of the marker genes of differentiated cells induced by both activin and RA at the end of step 2.
FIG. 2C shows the RT-PCR results of the expressions of the marker genes of differentiated cells at the end of step 3.

The result is shown in FIGS. 2A-2C, row one in FIG. 2A shows the result of using only activin A induction, and at the end of step 2, the cells thus treated mainly express hnf3β and pdx-1; row 2 shows the result of using only RA induction, and at the end of step 2, cells thus treated express only hnf3β. FIG. 2B shows the result of using both activin A and RA induction, and at the end of step 2, the cells thus treated express marker genes pdx-1, hnf3β, insulinI and hnf4α; FIG. 2C indicates at the end of step 3, cell induced by both activin A and RA mainly express insulinI, pdx-1, isl1, glut2 and hnf3 (lane 3 "+"). In FIGS. 2A-2C, –RT means there is no negative control for reverse transcription; blank means negative control in which only water is used. In FIG. 2C, "Pancreas" in lane 1 is the positive control for mature mice pancreatic cells; symbol "–" in lane 2 represents there is no activin A and RA induced mice ES-R1 cell at the end of step 3; symbol "+" represents there are activin A and RA induced mice ES-R1 cells at the end of step 3.

These cells did not express markers of other islet endocrine cells (non-β cell) such as glucagon or somatostatin. This result suggests that TGF-β and RA signals may be specific for pancreatic β cell development and maturation. The induction was found to be strictly activin A- and RA-dependent, as absence of either one of them resulted in almost no small cluster formation and the induced cells did not express or only weakly expressed insulin, pdx1, isl1, glut2 and hnf3β (see FIG. 2C lane 2). Moreover, we found that if the dishes were coated with laminin or gelatin, instead of matrigel, no cell clusters formed in the third step.

3. Immunohistochemistry Assay.

Figure 3:
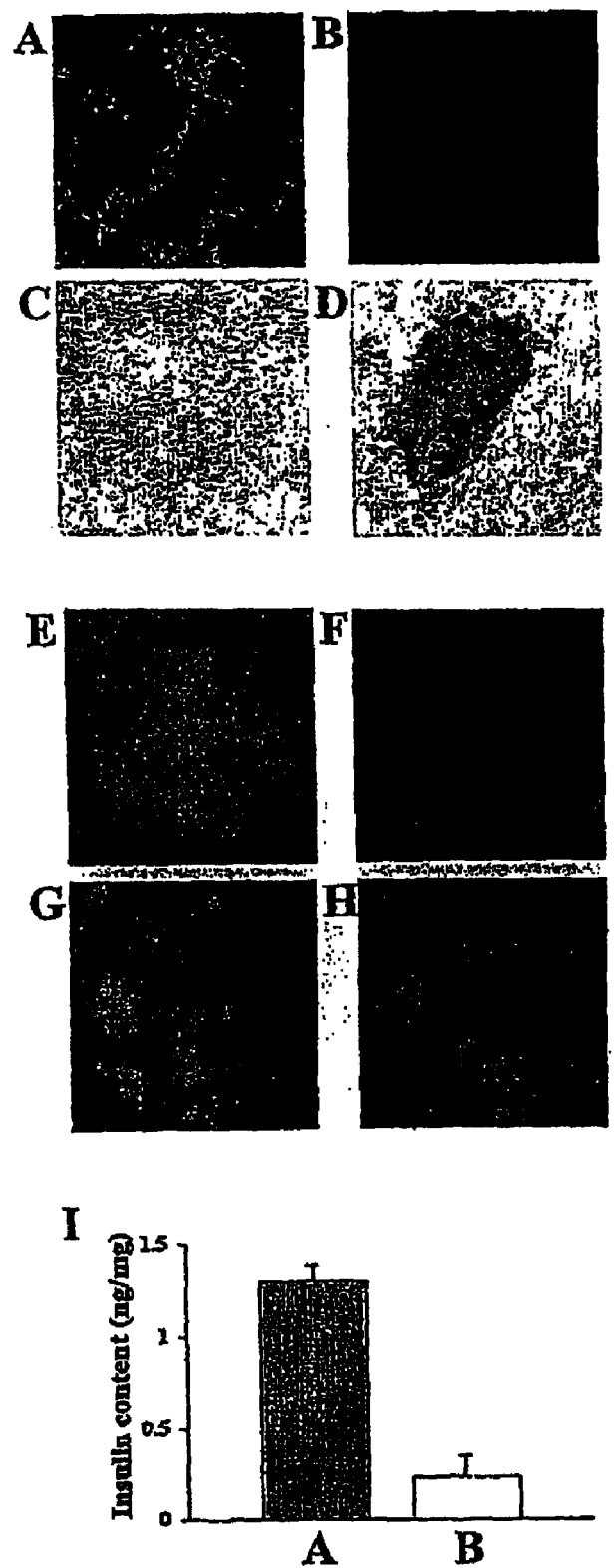
FIG. 3A shows the immunohistochemistry results of cells induced by the three-step approach stained with primary antibody to insulin.
FIG. 3B shows the immunohistochemistry results of cells induced by the three-step approach stained with primary antibody to C-peptide.
FIG. 3C shows the insulin diaminobenzidine tetrahydrochloride (DAB) staining results of cells without activin A and RA induction (200×).
FIG. 3D shows the insulin DAB staining results of cells with activin A and RA induction (200×).
FIGS. 3E and 3G show the expressions of EGFP in EGFP reporter-transfected ER-R1 cells which have been induced by the three-step approach, wherein E and G represent different structures (200×).
FIGS. 3F and 3H show the immunohistochemistry results of EGFP reporter-transfected ER-R1 cells which have been induced by the three-step approach stained with primary antibody to insulin, wherein F and H represent different structures (200×)
FIG. 3I shows the result of insulin release detected by ELISA.

Immunohistochemistry assay was taken to demonstrate induced insulin-positive cell can also express C-peptide: Induced cells in step 3 were fixed in 4% paraformaldehyde and washed three times by PBS, and then incubated with 10% normal goat serum or rabbit serum for 20 min at room temperature. Goat serum were removed, and the cells were incubated with primary antibody to insulin (Rabbit polyclonal IgG, 1:200, Santa Cruz) or to C-peptide (Linco) overnight at 4° C., and further incubated with secondary antibody Rhodamine-conjugated goat anti-rabbit IgG, FITC-conjugated rabbit anti-goat IgG (1:200, Santa Cruz) or biotin-conjugated IgG (work solution, Santa Cruz). DAB was utilized as reaction substrate when biotin-conjugated IgG was used as secondary antibody. Images were captured using an Olympus phase contrast microscope (Olympus IX-71). The result shows the cells can express both insulin and C-peptide (FIGS. 3A and 3B).

DTZ staining (Shiroi A, Yoshikawa M, Yokota H, et al. Identification of insulin-producing cells derived from embryonic stem cells by Zinc-Chelating Dithizone. STEM CELLS 2002; 20(4):284-292.) was used to test the cells developed by the three-step approach or cells developed without activin A and RA induction (control). The result indicated DTZ positive cell clusters (carmine) developed after the three-step treatment (FIG. 3D), but not in control group (FIG. 3C), which indicates the resultant cell clusters contain insulin-positive cells.

4. EGFP Reporter Construction and ES Cell Transfection.

Evidence shows the ES cell progeny could uptake insulin from culture medium and then could be stained positive by insulin antibody (Hori Y, Rulifson I C, Tsai B C, et al. Growth inhibitors promote differentiation of insulin-producing tissue from embryonic stem cells. Proc Natl Acad Sci USA 2002; 99(25):16105-16110). To confirm whether the insulin was actually generated by the induced clusters, an EGFP-reporter system was used to detect the insulin expression. R1 ES cells were transfected with an EGFP-reporter vector, in which a green fluorescent protein cDNA was driven by an insulin promoter. ES cells that have incorporated this vector were selected by G418 and induced with activin A and RA. The details are as follows: A human-insulin promoter-EGFP vector was constructed. A 0.4 kb Xba I and Hind III fragment containing human-insulin promoter from pFOXCAT-362 hIns (Odagiri H, Wang J H, and German M S. Function of the Human Insulin Promoter in Primary Cultured Islet Cells. THE JOURNAL OF BIOLOGICAL CHEMISTRY 1996; 271(4):1909-1915) was ligated to the pCMV-EGFPN3 (BD Biosciences) whose CMV promoter was removed by AseI-HinddIII digestion. This vector with neomycin resistance was transfected into the ES R1 cell line by electroporation and positive ES clones were selected with 250 µg/ml G418 (Gibco-BRL). The selected positive clones of mice ES-R1 were firstly stimulated by activin A and RA, then the resultant small cell clusters were detected by EGFP. The result of EGFP is shown in FIGS. 3E and 3G, in which the expression of EGFP can be detected in small cell clusters. Furthermore, the expression is corresponding to insulin expression (FIGS. 3F and 3H, detected by the immunohistochemistry method in step 3.). There data indicate the combination of activin A and RA, as well as other maturation factors can induce ES cells to differentiate into pancreatic cells.

5. Insulin Release Test by ELISA.

To further test whether the insulin release of induced cells was glucose-dependent, two glucose concentrations (5.5 mM and 27.7 mM) were used. Cells were preincubated with Krebs-Ringer buffer containing 2.5 mM glucose (pH 7.4) at 37° C. for 90 min. To induce insulin release, the cells were then incubated with Krebs-Ringer buffer with 27.7 mM glucose for 15 minutes at 37° C. (Sample A). Another group of cells were preincubated with Krebs-Ringer buffer containing 2.5 mM glucose at 37° C. for 90 min. To induce insulin release, the cells were then incubated with Krebs-Ringer buffer with 5.5 mM glucose for 15 minutes at 37° C. (Sample B, as control). Then the conditioned medium was collected. The two medium samples were tested for insulin release content by Rat/Mouse Insulin ELISA Kit (CRYSTAL CHEM NC). The total cell protein content was tested by BCA™ Protein Assay Kit (PIERCE). The results indicate the amount of released insulin under high glucose concentration is about 5 times higher than that under low glucose concentration (See FIG. 3I, the unit of insulin content is ng(insulin)/mg (total cell protein); column A shows the insulin level after treated with 27.7 mM glucose medium, which is nearly five times higher than that in column B (5.5 mM glucose medium)). The result indicates the secretion of insulin by insulin-positive cells derived from ES can also be regulated by glucose concentration.

6. Transplantation of Insulin-Producing Cells Under Renal Subcapsule.

Figure 4:
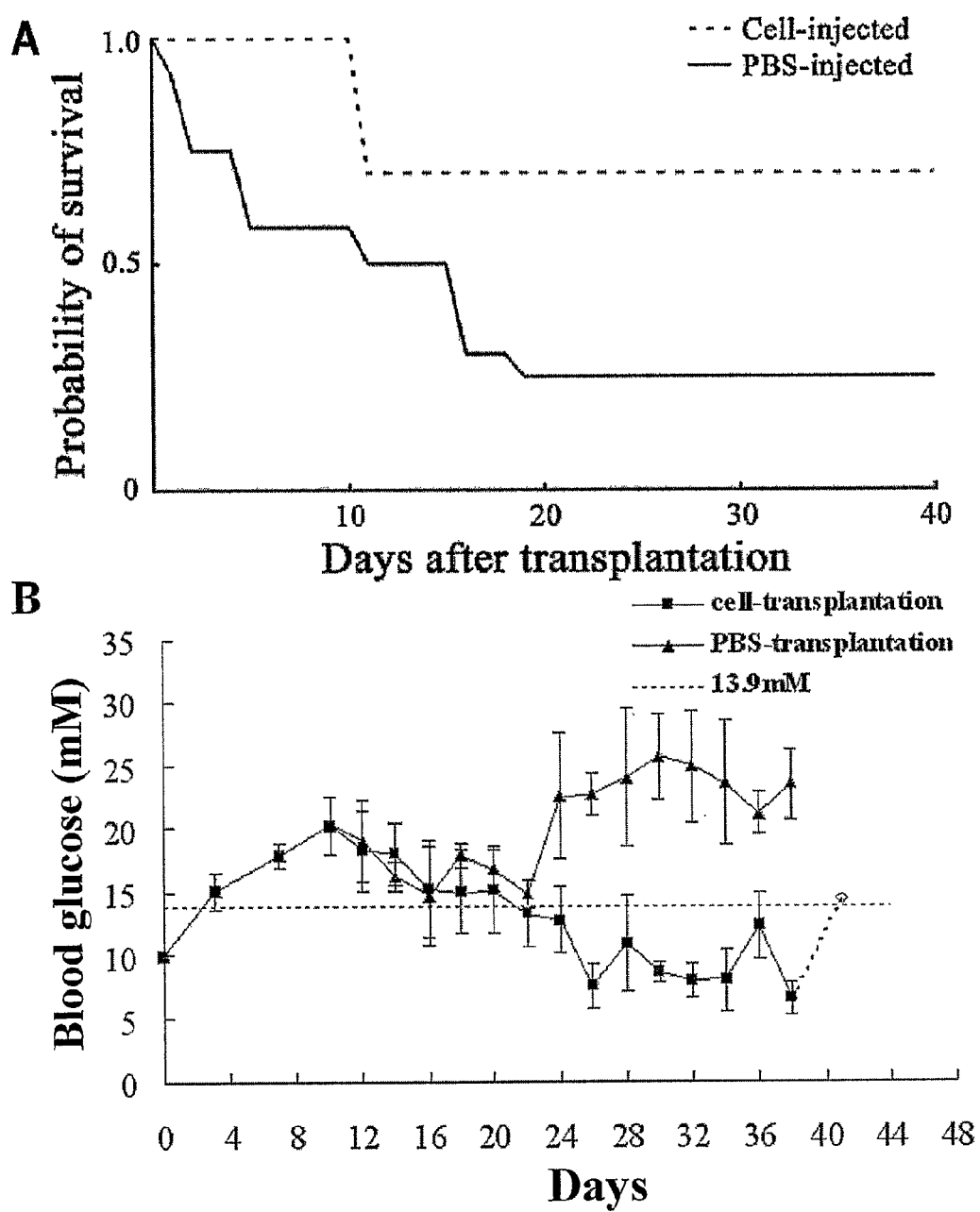
FIG. 4A shows the comparison of possibility of survival between differentiated cells-transplanted diabetic mice (n=9) and PBS-transplanted diabetic mice (n=12).
FIG. 4B shows the analysis of blood glucose level of differentiated cells transplanted diabetic mice (n=5) and PBS transplanted diabetic mice (n=3).
Figure 5:
FIG. 5A shows the immunohistochemistry results of insulin expression in PBS transplanted mice (200×).
FIG. 5B shows the immunohistochemistry results of insulin expression in differentiated cells-transplanted mice (200×).
Figure 5:

To test if insulin-positive cells derived from ES cells can rescue diabetic mice, the differentiated cells were transplanted into the left renal capsules of STZ-induced diabetic mice (n=9). Details are as follows:

Streptozotocin (STZ, Sigma) was injected by i. p. at 50 mg/kg into six to eight week old 129 male mice for 5 days to induce experimental diabetes before cell or PBS transplantation. When the blood glucose of STZ-treated mice was above 13.9 mM, $1\times10^6$ insulin-producing cells were transplanted into the left renal capsule. PBS treatment was acted as control (n=12). Blood glucose was measured by GlucoTREND2 (Roche) from snipped tail. Cryostat sections of the operated kidneys were prepared and insulin expression of transplanted cells in the renal capsule was tested by immunohistochemistry. The result indicates differentiated cells-treated diabetic mice (n=9) survived longer and the survival probability reached 70%, while survival probability of PBS-transplanted diabetic mice (n=12, real line) was 25% (FIG. 4A). Furthermore, the survival mice can maintain their body weight at normal level. About two weeks later, Blood glucose level of cell-transplanted diabetic mice came back to normal level (<13.9 mM); in contrast, the glucose level of PBS transplanted mice (n=3) still retained high blood glucose (>13.9 mM) (FIG. 4B). In addition, after the cell-transplanted left kidney was removed, the blood glucose level of the mice increased up to 14 mM. Insulin positive cells were not detected in PBS injected left kidney by primary antibody to insulin (FIG. 5A); insulin positive cells was detected only in the differentiated cell-treated kidney of STZ-diabetic mice (FIG. 5B). There results indicate insulin-positive cells derived from ES cells can rescue diabetic mice.

Example 2 Induction of Human Embryonic Stem Cells into Pancreatic Cells

Human ES cell line, H1 or H9 (Thomson J A, Itskovitz-Eldor J, Shapiro S S, et al. Embryonic Stem Cell Lines Derived from Human Blastocysts. Science 1998; 282:1145-1147.), were used in the present invention. The cells were cultured under 37° C.

The culture system is chemical defined medium (CDM: 50% IMDM (Gibco), 50% F12 (Gibco), monothioglycerol (sigma)450 uM, insulin-transferrin-seleninumA (ITS, Gibco), Albumin Fraction V (Sigma) 5 mg/ml). Briefly, hES cells are transferred into CDM for differentiation. Then, activin A and RA were used to induce hES cells into pancreatic progenitors. On this basis, islet culturing condition as described in mES induction approach is utilized to further mature hES-derived pancreatic β cell.

For differentiation, our protocol was designed as follows: in the first step, hES cells were passaged onto 1% Matrigel (B&D Biosciences)-coated tissue culture dishes (Nunc). Then, the culture medium was changed to modified CDM as described (11): 50% IMDM (Gibco) plus 50% F12 NUT-MIX (Gibco), supplemented with Insulin-Transferrin-Selenium-A (1:100, Gibco) and 450 μM of monothioglycerol (Sigma), and 5 mg/ml albumin fraction V (Sigma). Two days later, the cells were induced with CDM containing 50 ng/ml activin A (Sigma) for 4 days. In the second step, after 4 days of activin A induction, the cells were transferred into CDM with $10^{-6}$ M RA (Sigma) for another 4 days. In the third step, the culture medium was changed from CDM to modified islet maturation medium (12): DMEM/F12 (Gibco), Insulin-Transferrin-Selenium-A (1:100, Gibco) and 2 mg/ml albumin fraction V (Sigma) with 10 ng/ml bFGF (Invitrogen) for the first 3 days and with 10 mM nicotinamide (Sigma) for the next 2 days. The cells were then digested by 0.5 mg/ml dispase (Gibco) and transferred into Ultra Low Attachment culture dishes (Costar) for 5 days form suspension culture to achieve islet maturation.

2. RT-PCR Analysis of Gene Expression in Differentiated Cells.

The expression of somastatin (SST), Glut2, Amylase (Amy), Sox17, Hnf4α, pdx-1, Insulin (INS), Hb9, glucokinase(GCK), IFABP etc. in differentiated cells and control cells (cultured in CDM without activin A and RA induction) were detected by RT-PCR, according to the method described in section 2 of example 1. Here, differentiated cell refers to maturation p cells obtained by following the three-step method. Control cells refer to cells which have been induced by either activin A or RA. The sequences for the PCR primers (sense and antisense, respectively) are:

```
gapd:
GTCATTGAGAGCAATGCCAG                        (SEQ ID No. 15)
and

GTGTTCCTACCCCCAATGTG (200 bp);              (SEQ ID No. 16)

sox17:
CAGTGACGACCAGAGCCAGACC                      (SEQ ID No. 17)
and

CCACGACTTGCCCAGCATCTT (292 bp);             (SEQ ID No. 18)

pdx1:
ACCAAAGCTCACGCGTGGAAA                       (SEQ ID No. 19)
and

TGATGTGTCTCTCGGTCAAGTT (200 bp);            (SEQ ID No. 20)

hlxb9:
CCTAAGATGCCCGACTTCAACTCCC                   (SEQ ID No. 21)
and

GCCCTTCTGTTTCTCCGCTTCCTG (276 bp);          (SEQ ID No. 22)

hnf4α:
ATCAGAAGGCACCAACCTCAAC                      (SEQ ID No. 23)
and

TGTCTTTGTCCACCACGCACT (197 bp);             (SEQ ID No. 24)

insulin:
GAGGCCATCAAGCACCATCAC                       (SEQ ID No. 25)
and

GGCTGCGTCTAGTTGCAGTA (373 bp);              (SEQ ID No. 26)

glut2:
GCTACCGACAGCCTATTCTA                        (SEQ ID No. 27)
and

CAAGTCCACTGACATGAAG (267 bp);               (SEQ ID No. 28)

amylase (amy):
CTGACAACTTCAAAGCAAA                         (SEQ ID No. 29)
and

TACAGCATCCACATAAATACGA (358 bp);            (SEQ ID No. 30)

somatostatin (SST):
GATGCTGTCCTGCCGCCTCC                        (SEQ ID No. 31)
and TGCCATAGCCGGGTTTGA (292 bp);                (SEQ ID No. 32)

sur1:
TTGCCGAAACCGTAGAAGGA                        (SEQ ID No. 33)
and

TTGGAGACCATTAGGGCGTAG (268 bp);             (SEQ ID No. 34)

glucagon (GCG):
AGGCAGACCCACTCAGTGA                         (SEQ ID No. 35)
and

AACAATGGCGACCTCTTCTG (308 bp);              (SEQ ID No. 36)

glucokinase (GCK):
AGGGAATGCTTGCCGACTC                         (SEQ ID No. 37)
and CACTGGCCTCTTCATGGGT (375 bp).               (SEQ ID No. 38)
```

The results are shown in FIGS. 7A and 7B, which indicate differentiated Es cells can express the marker genes of maturation β cells such as insulinI, pdx-1, glucokinase and glut2 (FIG. 7A). In contrast, the control group basically does not express any of the marker gene (FIG. 7B).

3. Immunohistochemistry Assay.

Induced cells were fixed in 4% paraformaldehyde and washed three times by PBS, then incubated with PBS containing 0.3% tritonX-100 (Sigma) and 10% normal serum for 40 mins at room temperature. The cells were then incubated with primary antibody to Goat anti-human sox17 antibody (1:40, R&D SYSTEMS), Mouse anti-human insulin monoclonal antibody (1:100, CHEMICON), Rabbit anti-human C-peptide antibody (1:200, Linco), glucagon (Goat polygonal IgG, 1:200, Santa Cruz), pdx1 (Goat polyclonal IgG, 1:200, Santa Cruz), amylase (Rabbit polygonal IgG, 1:500, Sigma), ngn3 (Goat polyclonal IgG, 1:200, Santa Cruz) or somatostatin (Goat polyclonal IgG, 1:200, Santa Cruz) overnight at 4° C., and further incubated with secondary antibody respectively: TRITC-conjugated goat anti-rabbit IgG, FITC-conjugated rabbit anti-goat IgG, FITC-conjugated Goat anti-Mouse IgG, FITC-conjugated Donkey anti-goat IgG or TRITC-conjugated Donkey anti-rabbit IgG (1:200, all from Jackson ImmunoResearch, INC.). Nuclei were detected by DAPI (Sigma) staining. Images were captured using an Olympus phase contrast microscope (Olympus IX-71). The percent of C-peptide positive cells was calculated with Image-Pro Plus software (Media Cybernetics).

The results show the cells can express pancreatic beta cell genes such as C-peptide, pdx-1 etc (FIG. 8).

4. Transplantation of Insulin-Producing Cells Under Renal Subcapsule.

To test if insulin-positive cells derived from ES cells can normally function in vivo, the differentiated cells were transplanted into the left renal capsules of STZ-induced diabetic mice (n=12). Details are as follows:

The Institutional Animal Care and Use Committees of Peking University approved all animal procedures. Streptozotocin (STZ, Sigma) was injected i. p. at 40 mg/kg into 4-6 week-old BALB/c male nude mice for 5 days to induce experimental diabetes before cells or PBS transplantation. When the STZ-treated mice had developed diabetes, about $1 \times 10^6$ induced cells were transplanted into the left renal capsule. PBS or cells without activin A and RA induction were used as control. A glucose tolerance test was performed by i.g. glucose (2.5 g kg$^{-1}$ body weight) after overnight fasting. Blood glucose was measured by GlucoTREND2 (Roche) from snipped tail. Cryostat sections of the operated kidneys were prepared and C-peptide expression of the renal capsule transplanted cells was confirmed by immunohistochemistry. The hES-derived cells were detected by Mouse anti-human nuclei monoclonal antibody (1:30, CHEMICON). Images were captured using an Olympus phase contrast microscope (Olympus IX-71). The results show insulin positive cells were not detected in PBS injected kidney; the results from transplanted mice were shown in FIGS. 11A and 11B. Transplanted human ES-derived differentiated cells can express C-peptide (FIG. 11A). The C-peptide positive cells can be stained by antibodies specific to human nuclear, indicating the cells are derived from human ES cells (FIG. 11B).

Experimental induction of human embryonic stem (hES) cells to become pancreatic β cells is a potential source for cell transplantation therapy of type I diabetes mellitus. The three-step approach provided here is able to induce hES to differentiate into functional insulin-producing cells. This method, which is based on culturing hES in chemically defined medium (CDM) with activin A, all-trans retinoic acid (RA) and other maturation factors (see FIG. 6), mimics the signaling of pancreas development in vivo. The hES-derived cells express pancreatic β cell markers such as pdx1, insulin, glucokinase and glut2 by RT-PCR test (see FIG. 7). These cells are C-peptide, pdx1, glucagon, somatostatin or amylase positive, and C-peptide positive excludes the possibility of insulin uptake by immunohistochemistry test (see FIG. 8). To further test whether the insulin release of induced cells was glucose-dependent, two glucose concentrations (2.5 mM and 27.5 mM) were used. After pre-incubated with Krebs-Ringer buffer at 37° C. for 90 min, the cells were first incubated with Krebs-Ringer buffer containing 2.5 mM glucose at 37° C. for 15 minutes. To induce insulin release, the cells were incubated with 27.5 mM glucose for another 15 minutes. Then the respective conditioned mediums were collected. The two medium samples were tested for insulin release content with a Rat/Mouse Insulin ELISA Kit (Linco). The intracellular C-peptide concentration was detected with a Human C-peptide ELISA Kit (Linco). The total cell protein content was tested with a BCA™ Protein Assay Kit (PIERCE). We found that for the cells induced in the suspension culture, the insulin secretion was increase by 200% in the high glucose medium compared to the low glucose medium (FIG. 9A). Moreover, the intracellular C-peptide content was also increased in the cells produced with the suspension culture (FIG. 9B). However, insulin secretion from the cells in the adhesion culture did not respond to glucose stimulation (FIGS. 9A, B). These data indicated that the suspension culture resulted in more efficient maturation of islet-like cells than the adhesion culture.

To investigate whether the induced cells could function in vivo, we transplanted the differentiated cells under the renal capsules of diabetic nude mice. The blood glucose of 30% of the induced cell-transplanted mice was maintained at normal levels (<13.9 mM) for nearly six weeks (FIG. 10A). The glucose tolerance test indicated that these 30% blood glucose rescued nude mice also attained improved glucose regulation capability compared to that of control-operated mice (FIG. 10B). One month after transplantation, C-peptide positive cells were detected in the kidney capsules transplanted with the cells induced by the three-stage approach. These cells were stained by human nuclei specific antibody, which indicated that these C-peptide positive cells were derived from the injected hES cells (FIGS. 11A and 11B).

These results clearly showed that the hES cell-derived insulin-producing cells were not only able to survive; they rescued 30% of STZ-induced diabetic mice in vivo. The findings reported here offer a novel in vitro model to study the development mechanism of human islet cells and these hES-derived insulin-producing cells may be utilized in future for transplantation therapy of type I diabetes mellitus.

What is claimed is:

1. A method for inducing human or mouse embryonic stem cells to develop into insulin-producing cells, comprising in sequence the steps of:
   (a) coating a culture vessel with Matrigel®;
   (b) culturing the embryonic stem cells in the Matrigel®-coated culture vessel containing a cell culture medium to form embryonic bodies;
   (c) culturing embryonic body cells from the embryonic bodies from step (b) with Activin A to form differentiated cells;
   (d) incubating the differentiated cells from step (c) with retinoid acid (RA); and
   (e) incubating the differentiated cells from step (d) with bFGF to develop into the insulin-producing cells.

2. The method of claim 1, wherein the concentration of Activin A is about 50-300 ng/ml culture medium; and the concentration of RA is about $1\times10^{-7}$-$1\times10^{-5}$ mol/L culture medium.

3. The method of claim 1, wherein the mass percentage of the Matrigel® is about 1% of the cell culture medium.

4. The method of claim 3, wherein the embryonic body cells are incubated with Activin A for 20 hours-4 days, then cultured in a culture medium without Activin A for 6-8 hours, and then incubated with RA for 20 hours-4 days to develop into the insulin-producing cells.

5. The method of claim 4, wherein the concentration of bFGF is 8-12 ng/ml.

6. The method of claim 5, further comprising the step of incubating the expanded insulin-producing cells in a culture medium containing N2 supplement, B27 supplement, laminin, and nicotinamide.

7. The method of claim 6, wherein the culture medium for incubating the expanded insulin-producing cells is DMEM/F12 or CDM containing N2 supplement, B27 supplement, 1 µg/ml of laminin, 10 ng/ml of bFGF, Insulin-Transferrin-Selenium-A (1:100) and 10 mmol/L of nicotinamide.

* * * * *